United States Patent [19]

Smoot

[11] 4,005,359
[45] Jan. 25, 1977

[54] RESONANT FREQUENCY MEASURING DEVICE FOR GAUGING COATING THICKNESS

[76] Inventor: William N. Smoot, 9 E. Irving St., Chevy Chase, Md. 20015

[22] Filed: Nov. 7, 1975

[21] Appl. No.: 629,742

[52] U.S. Cl. .......................................... 324/34 TK
[51] Int. Cl.² .................. G01R 33/00; G01R 33/12
[58] Field of Search .............. 324/34 TK, 40, 41, 3

[56] References Cited

UNITED STATES PATENTS

| | | | |
|---|---|---|---|
| 1,792,249 | 2/1931 | Serduke | 324/34 TK |
| 2,154,156 | 4/1939 | Turner et al. | 324/40 |
| 2,189,092 | 2/1940 | Urmenyi | 324/40 |
| 2,237,254 | 4/1941 | Broekhuysen | 324/40 X |
| 2,267,884 | 12/1941 | Zuschlag | 324/40 |
| 2,572,908 | 10/1951 | Brenholdt | 324/34 TK |
| 2,875,429 | 2/1959 | Quade | 324/41 |

FOREIGN PATENTS OR APPLICATIONS 1,237,335    3/1967    Germany .................... 324/34 TK

OTHER PUBLICATIONS

Hoel, J. E., *Magnetic Reluctance, Film Thickness Gauge*, IBM Tech. Discl. Bull., vol. 13, No. 10, Mar. 1971, pp. 3048, 3049.

*Primary Examiner*—Strecker Gerard R.
*Attorney, Agent, or Firm*—R. Sciascia; R. Beers; S. Sheinbein

[57] ABSTRACT

An electronic thickness gauge for measuring the coating thickness over magnetic and over conductive, non-magnetic substrates by measuring the movement of the low-frequency hump in the response curve for an overcoupled, double-tuned, open-faced transformer when the above-mentioned substrates are placed across the gap between the transformer pole-faces.

4 Claims, 13 Drawing Figures

FIG.4
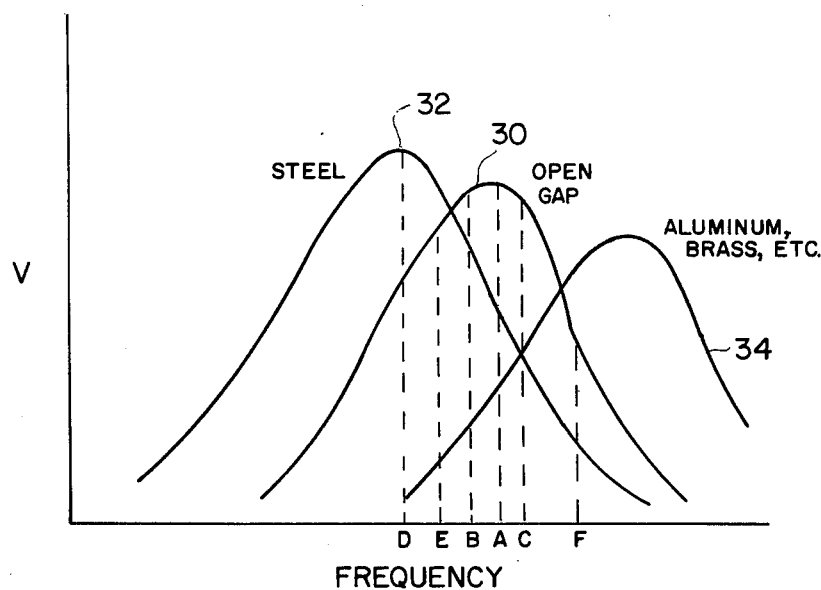
FIG.5A
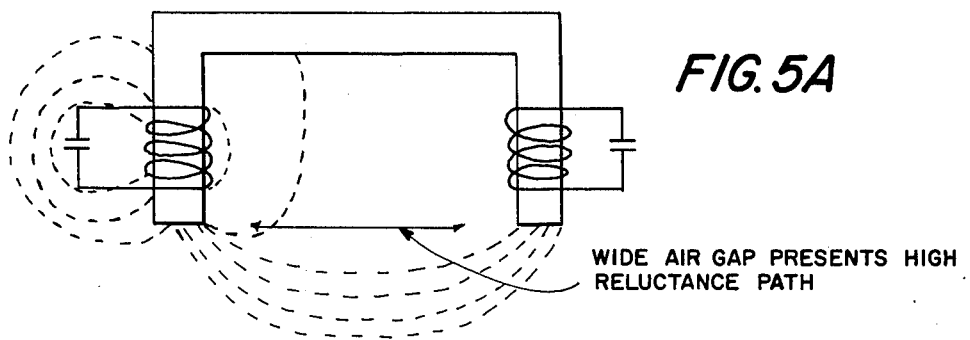
WIDE AIR GAP PRESENTS HIGH RELUCTANCE PATH
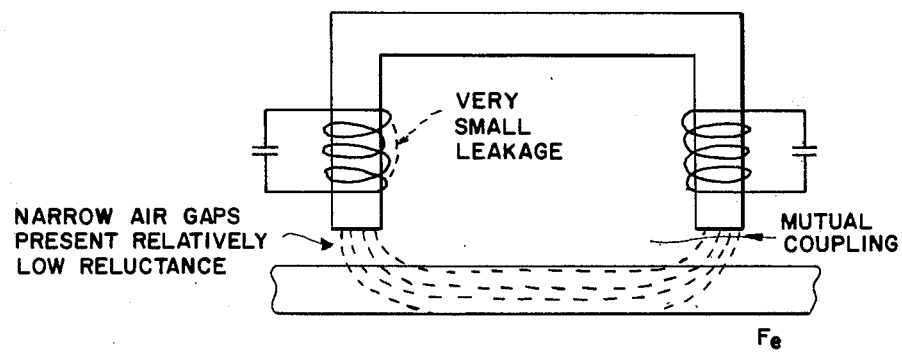
VERY SMALL LEAKAGE
NARROW AIR GAPS PRESENT RELATIVELY LOW RELUCTANCE
MUTUAL COUPLING
Fe
FIG.5B

MUTUAL COUPLING
REDUCED (30%–40%.)

EDDY

LINES OF FLUX OF VARYING INTENSITY
DO NOT PENETRATE CONDUCTIVE
MATERIALS, DUE TO EDDY CURRENTS.

MUTUAL COUPLING
FLUX

RESONANT FREQUENCY MEASURING DEVICE FOR GAUGING COATING THICKNESS

FIELD OF THE INVENTION

The present invention relates generally to coating-thickness gauges and more particularly to an electronic, resonant-frequency-measuring device for gauging a coating thickness.

BACKGROUND OF THE INVENTION

When an opaque coating such as paint, tile, or terrazzo is applied to a surface, it is usually impossible to determine, by observation of the coating, its thickness. Thickness is important for several reasons. For example, a coating of improper thickness may not perform properly, may not adhere well, or may crack or flake. An excess of organic material represents a definite increase in fire hazard, even when materials of low flammability are used. Aboard ship, an excess of coating material means excess weight, which can be quite significant if deck tile is several layers thick.

Because of the problems of improper thickness, there is a need for a simple, non-destructive means of measuring the thickness of shipboard coatings. The ideal device should be rugged and portable, should be effective whether the coating is over steel or aluminum, and should be useful for typical coatings at typical thicknesses, such as paint (a fraction of a millimeter), tile (a few millimeters), or terrazzo (1 or 2 centimeters). Precision is desirable, but not of great importance, since errors of several percent are not usually very significant.

SUMMARY OF THE INVENTION

The present invention is a reasonably simple instrument which meets the above requirements. The basic component of the instrument is a double-tuned, open-core, significantly overcoupled transformer with an A.C. input to its primary winding and with a voltage measuring device, which may be specialized to the desired scale, connected to the secondary winding of the transformer. The open core of magnetic material makes the transformer sensitive to metallic materials near the air gap of the open core, but not sensitive elsewhere. The double tuning of the transformer makes its secondary output very sensitive to changes in the inductance of the circuit. This sensitivity is evidenced by the changes of the resonant-frequency response of the tuned circuits with changes in inductance. Finally, the very tight coupling of the transformer windings makes the output of its secondary winding sensitive to small changes in coupling. This is evidenced by changes in the simple transformer action and, more importantly, by changes in the resonant-frequency response characteristics of the double-tuned transformer. This change in the resonant-frequency characteristic when magnetic and conductive non-magnetic materials are brought into close proximity to the open core of the transformer caused, in part, by the change in inductance in the tuned circuits but, primarily, by the change in coupling of the transformer windings, may be accurately measured to provide a gauge for the coating thickness on said magnetic and non-magnetic conductive materials.

The electronic gauge of the present invention is further comprised of a feedback network so that the output response of the secondary winding of the transformer may be utilized to control the frequency of the A.C. input to the primary winding. The feedback circuit substantially increases the range of the device.

OBJECTS OF THE INVENTION

An object of the present invention is to accurately gauge the thickness of a coating on a magnetic or on a conductive, non-magnetic material.

A further object of the present invention is to provide a coating-thickness gauge for magnetic and conductive, non-magnetic substrates which is accurate over a large range of thicknesses and is portable.

Other objects, advantages, and novel features of the present invention will become apparent from the following detailed description of the invention when considered in conjunction with the accompanying drawings.

BRIEF DESCRIPTION OF THE DRAWINGS

FIG. 1b is voltage vs. frequency graphical diagram of the response of the circuit of FIG. 1a.

FIG. 4 is a voltage vs. frequency graphical representation of the response of the circuit of FIG. 3 to steel, open, and aluminum gapping of the core.

FIG. 5a is a schematic diagram of the transformer core with an open gap and illustrating the flux coupling lines in this situation.

FIG. 5b is a schematic diagram of the transformer core gapped with a steel plate and illustrating the flux coupling lines.

DETAILED DESCRIPTION OF THE INVENTION

The physical principle upon which the present invention is based is described first, followed thereafter by a description of the practical instrument.

Figure 1A:
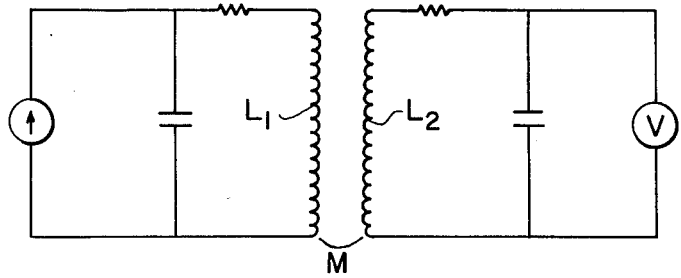
FIG. 1a is a schematic diagram of a typical double-tuned radio circuit.
Figure 1B:
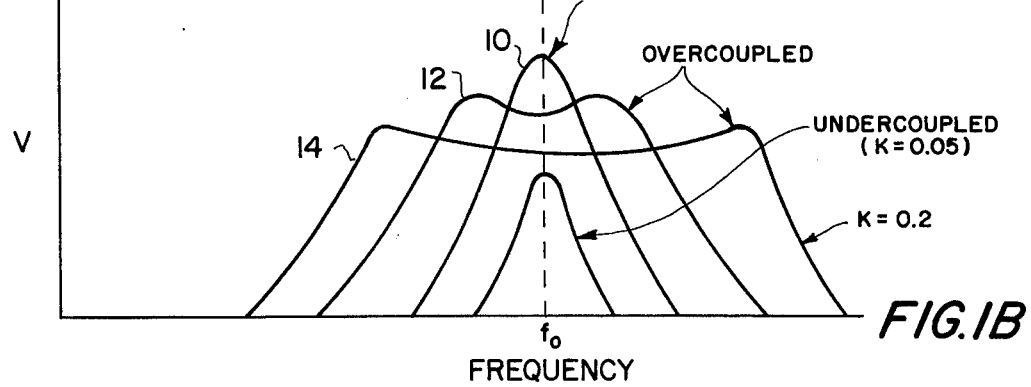

Double-tuned transformer circuts such as the one shown in FIG. 1a are well-known in the electrical arts and are usually described in standard textbooks and handbooks in the context of radio communication systems. Such circuits are usually discussed in combination with the voltage vs. frequency response curves of FIG. 1b which show the influence of the coupling factor $k$ ($k = M/\sqrt{L_1 L_2}$, where $M$ is the mutual inductance of the transformer and $L_1$ and $L_2$ represent the inductances of the transformer windings) on circuit characteristics. Both halves of the circuit are tuned to the same frequency $f_o$. When the coupling of the windings is increased beyond critical coupling (point of maximum energy transfer between the windings, curve 10 in FIG. 1b), the frequency response begins to divide into two equal humps equally spaced about $f_o$. As coupling is increased further, the humps of frequency response separate even more and decrease in amplitude (curves 12 and 14). The curve 14, due to its approximately flat, wide top, is used in modulated-carrier communication systems. For this reason, most of the work done on this circuitry concerns itself with this coupling region. The circuits with response curves like those shown in FIG. 1b are generally referred to as sharply tuned (high - Q) circuits with loose coupling.

Figure 2:
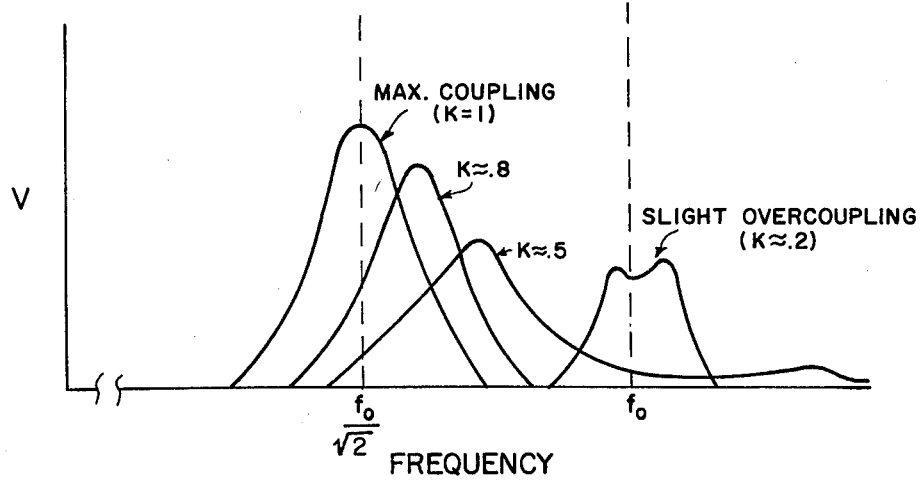
FIG. 2 is a voltage vs. frequency graphical representation of the circuit of FIG. 1a under a variety of tight coupling situations.

FIG. 2 shows the voltage vs. frequency response for the circuit of FIG. 1a when it is tightly coupled. As coupling is increased from the low values of FIG. 1b, the two humps are neither equal, nor equally spaced about $f_o$. The low-frequency hump grows again, and eventually is centered about $f_o/\sqrt{2}$ when unity coupling ($k=1$) is achieved. The high-frequency hump gets broader and lower and farther away from $f_o$, and ultimately disappears entirely at slightly less than unity coupling. Both effects are to be expected, for with unity coupling the circuit behaves as a perfect transformer, equivalent to a single-tuned circuit. The secondary load is reflected into the primary, doubling the effective primary capacitance, but not the primary inductance (only uncoupled or leakage inductance is reflected), thus making the new resonant frequency $(1/\sqrt{2})f_o$.

The significance of the effect described above, and depicted in FIG. 2, is that a change in coupling coefficient in a highly-overcoupled, double-tuned circuit, is equivalent to a change in tuning of a single-tuned circuit. That is, since the high-frequency hump in the response has disappeared, the center frequency of the low-frequency hump can be thought of as the tuning frequency. Thus, since a change in the coupling causes a change in the center frequency of the low-frequency hump, it can be considered to have caused a change in the tuning frequency of the entire circuit response. This relationship of the coupling of the windings to the center frequency of the low-frequency hump is the basis of the present invention.

Figure 3:
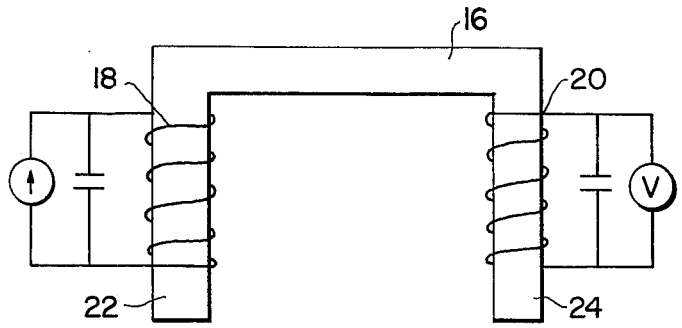
FIG. 3 is a schematic diagram of the open-core, overcoupled, double-tuned transformer of the present invention.

FIG. 3 shows an embodiment of a double-tuned overcoupled transformer which may be utilized to implement the present invention. The magnetic core 16 has a U shape with windings 18 and 20 wound around the arms 22 and 24, respectively, of the core 16. When nothing is placed across the open face of the U-shaped core, then the circuit has a response like that shown in curve 30 of FIG. 4. When a magnetic material such as a steel plate is placed flush across the gap of the open-faced core 16, the peak frequency response of the low-frequency hump of the circuit is substantially lowered and the height of the peak is raised to some extent as shown by the curve 32 of FIG. 4. This peak-frequency decrease is due to the fact that both the self inductance of the coils 18 and 20 and their mutual inductance are increased by the steel plate. The self inductance of the coils is increased because a greater proportion of magnetic material in the magnetic circuit permits more magnetic flux to be generated by current in a coil. The mutual coupling between the coils is, of course, increased since a greater proportion of the magnetic flux is confined to the magnetic material and thus links both of the coils. The actual peak response of the low-frequency hump relates to the self and mutual inductances according to the following equation:

$$\frac{\text{Frequency at peak of secondary voltage}}{\text{Resonant frequency of tuned circuits}} = \frac{1}{\sqrt{1 + k\left[1 - \frac{k_c^2}{2k^2}\left(\frac{Q_p}{Q_s} + \frac{Q_s}{Q_p}\right)\right]^{1/2}}}$$

where $k = \dfrac{M}{\sqrt{L_p L_s}}$ $M$ = mutual inductance
$L_p$ = total inductance of the primary winding
$L_s$ = total inductance of the secondary winding $Q_p = \dfrac{\omega L_p}{R_p}$ for the primary $Q_s = \dfrac{\omega L_s}{R_s}$ for the secondary $\omega = 2\pi$ times the frequency $k_c$ = critical coefficient of coupling = $1/\sqrt{Q_p Q_s}$
$R_p$ = resistance in the primary winding
$R_s$ = resistance in the secondary winding
The right side of the equation reduces to $1/\sqrt{2}$ when both $Q_p$ and $Q_s$ are very large.

FIG. 5a illustrates the flux paths from one pole for the double-tuned, over coupled circuit of FIG. 3 with an open gap. The figure evidences a substantial amount of leakage flux. FIG. 5b illustrates the flux paths from one pole for the same circuit with a steel plate across the gap. As can be seen from the figure, most of the flux lines are constrained within the steel plate so as to link both coils. This increase in the mutual inductance in conjunction with the self-inductance increase lowers the peak response frequency of the low-frequency hump in accordance with the foregoing equation. The resonant frequency of the individual tuned circuits is also lowered.

The curve 32 of FIG. 4 for a steel gap retains its shape and peak-frequency location with a given double-tuned transformer circuit for steel plate thicknesses exceeding approximately one-tenth of an inch (assuming a good steel-transformer core contact). If the steel plate has a coating over its surface, then there is not direct contact between the steel plate and the core, and thus the coupling is reduced between the windings. As the coupling is reduced, the curve 32 moves along the frequency scale toward the open gap curve 30. The thicker the coating, the larger the non-magnetic gap between the steel and the core, the more the coupling (relative to a good contact steel plate gap) decreases between the windings, and the higher the peak frequency of the curve 32 moves.

This coupling variation is the principal cause of the peak-frequency variation. A second, less significant, cause of the peak-frequency variation is the change in self-inductance of the windings as stated previously. Since an increase in coating thickness reduces the effect of the added flux caused by the bridging of the gap directly with a steel plate, the self-inductance will accordingly vary with the thickness of the coating and thus so will the peak frequency of the hump. This frequency variation is in the same direction as the frequency variation caused by the coupling change.

These two effects, the self-inductance variation and the coupling variation, combine to cause the peak frequency of the hump to vary significantly with the thickness of the coatings on the steel plate. Clearly, if this peak frequency or hump movement is properly calibrated, it can be utilized as a means of measuring the coating thickness over any magnetic material which will provide a good coupling bridge.

Figure 5C:
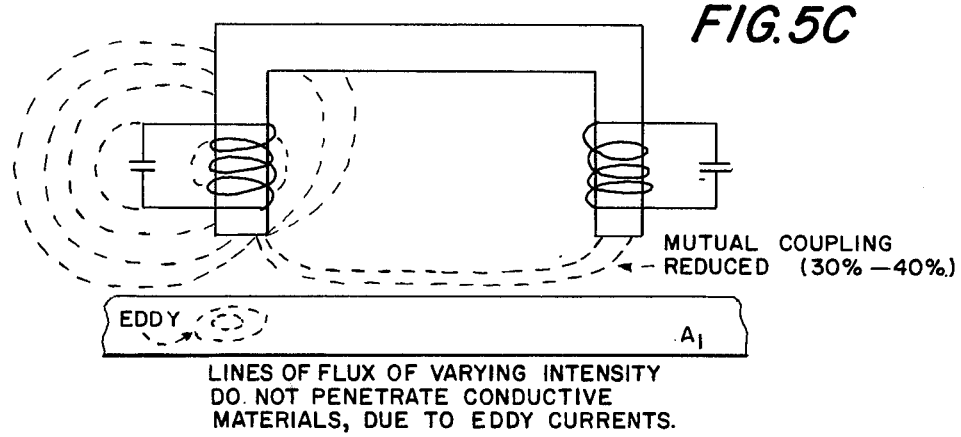
FIG. 5c is a schematic diagram of the transformer core gapped with aluminum and illustrating the flux coupling lines for this configuration.

When a conductive, non-magnetic material is placed across the core gap, it has the opposite effect from that of a magnetic plate gap. This is because a conductive, non-magnetic bridge such as an aluminum or brass plate acts as a partial magnetic shield between the pole faces of the core (since the eddy currents developed in the conductive, non-magnetic substrate by the magnetic field prevent the flux lines from penetrating the conductive material) thus spreading-out the flux linkages and thereby decreasing the coupling between the windings. The flux paths for an over-coupled double-tuned transformer with an aluminum plate bridging the gap between the arms are shown in FIG. 5c. In addition, the aluminum plate acts as a short-circuited turn on each winding, thus reducing the self-inductance in each winding. Accordingly, these two effects increase the peak frequency of the hump response and lower its amplitude slightly. This can be seen by an inspection of the curve 34 of FIG. 4 which represents the response of the transformer of FIG. 3 gapped with aluminum. Again, the aluminum-gap curve 34 will not vary for aluminum plate thicknesses over approximately one-tenth of an inch.

A coating on the aluminum plate will, of course, decrease this coupling and self-inductance change by an amount directly related to the thickness of the coating. Thus, the peak frequency or hump position on the frequency scale will vary with the thickness of the coating. Clearly, this peak frequency or hump movement can also be properly calibrated to provide an accurate coating-thickness measurement.

Figure 6A:
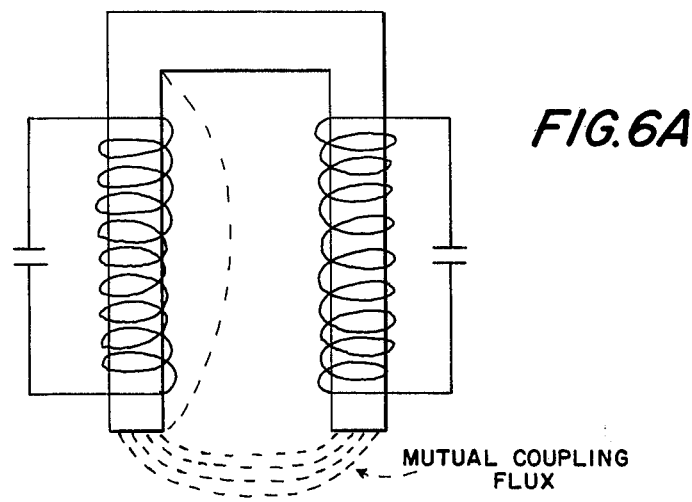
FIG. 6a is a schematic diagram illustrating the mutual flux coupling of a double-tuned, highly over-coupled transformer core.

From the above it is clear that the transformer windings 18 and 20 must be overcoupled in order to obtain the desired circuit response. There are a variety of methods of varying the coupling in a transformer to obtain this condition. For example, the pole gap in the yoke can be varied in relation to the pole arm length. FIG. 6a shows a transformer core in the shape of a rectangle with the short side open to form the pole gap. The narrow gap provides a relatively high coupling because the best path for the flux lines is from pole to pole. Since the mutual coupling is already so high, it cannot be increased much more even with the introduction of a steel plate across the pole gaps. Thus the range of sensitivity is very small.

Figure 6B:
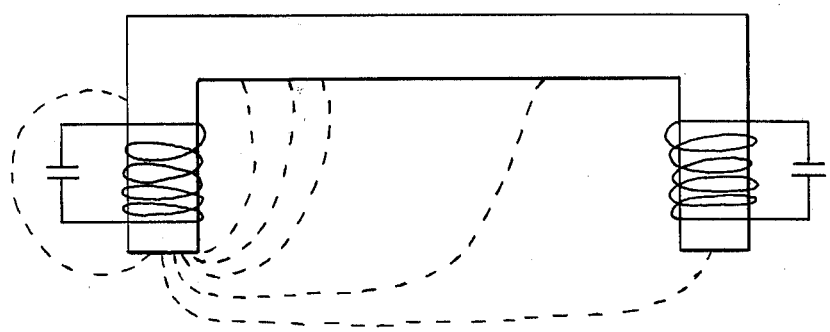
FIG. 6b is a schematic diagram illustrating the mutual flux coupling of a double-tuned, approximately critically coupled transformer core.

FIG. 6b shows a transformer core in the shape of a rectangle with the long side open to form the pole gap. The wide gap provides very little coupling, as is shown in the figure, due to the fact that the best path for the flux lines is from pole to cross bar. In the extreme case (a very wide pole separation), there is no coupling at all.

An open square design for the core has been found to be a satisfactory middle ground between these two extremes. It provides a sufficient flux coupling to make the windings substantially overcoupled, while providing enough leakage flux so that there can be a significant increase when a magnetic plate is placed across the pole faces.

There are, of course, a variety of other methods of varying the coupling. For example, air gaps might be introduced between the legs or arms and the bridge of the core.

By way of example only, the core used to implement the present embodiment is made from three stacks of straight pieces connected in the shape of a U. The stacks have a length of 2.25 inches, a 7/16 inch lamination width with a ¼ inch depth. The pole separation is 3 inches.

It should be understood that the core is not constrained to a U shape. But, it must have two arms which are joined in some fashion. However, these arms need not be parallel.

The actual numerical coupling required for a given application will, of course, depend upon the component selection for the reset of the circuitry. Generally, with a critical coupling of 5 to 10%, a coupling of 60 to 80% is required in order to remove the high-frequency hump from the circuit response as discussed previously. But, a coupling of 30 to 40% would be sufficient if the tuning of the circuit is sharp (i.e., the critical coupling is small).

Figure 7:
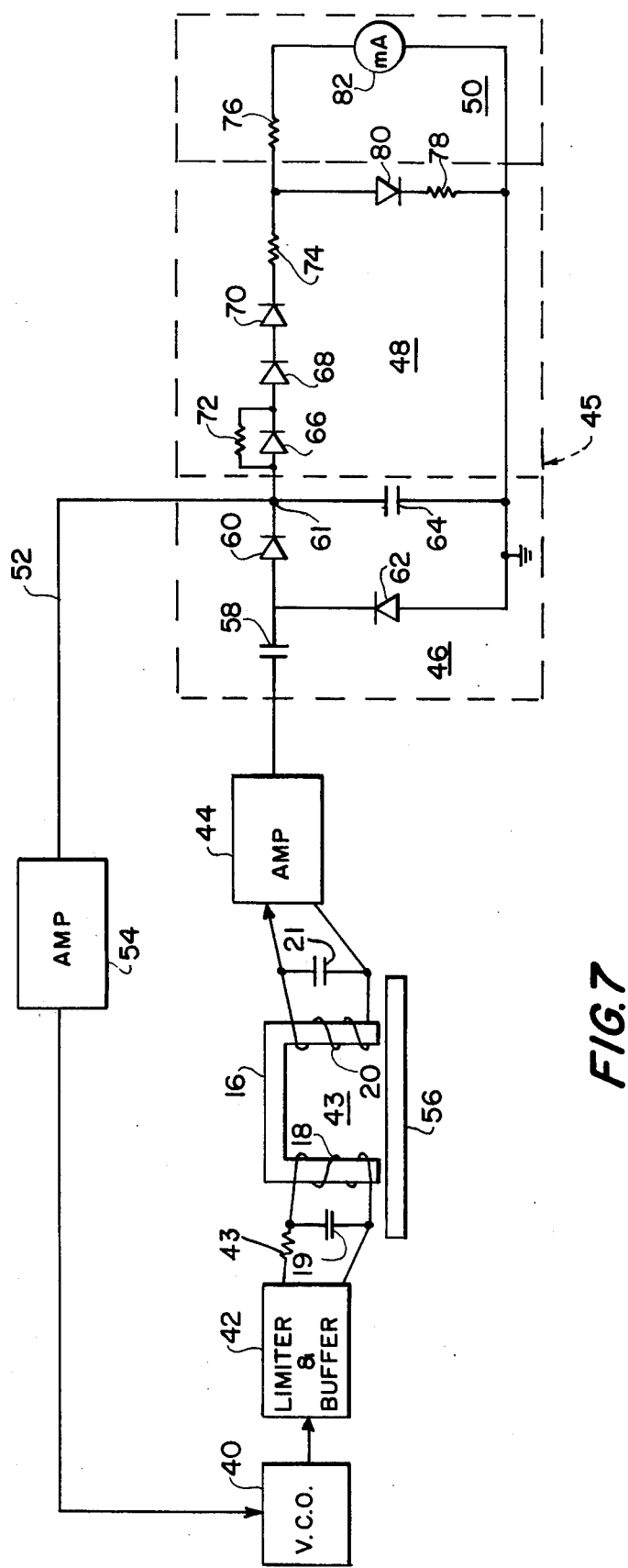
FIG. 7 is a schematic circuit diagram of one embodiment of the present invention.

The above principles are reduced to practice in FIG. 7. A voltage-controlled oscillator (VCO) 40 sets the operating frequency of the signal which is to be applied to the sensing transformer 43. This signal is applied to the transformer 43 by way of a limiter and buffer amplifier 42 which ensures the constant drive amplitude to the primary winding 18 of the transformer while isolating the VCO from the transformer. The capacitors 19 and 21 are connected across the primary and secondary windings 18 and 20, respectively, to provide a double-tuned transformer circuit. Resistor 43 adjusts the Q of the primary circuit. The secondary winding 20 connects to a low-gain operational amplifier 44 which provides isolation between the transformer secondary and the rest of the circuitry. The output from the amplifier 44 is applied to a calibrated measuring circuit 45, the reading from which may be used to determine coating thickness on the surface of a conductive, non-magnetic or a magnetic plate 56.

In the present embodiment, the measuring circuit 45 comprises the following components: a rectifier and voltage-doubler circuit 46 which rectifies, voltage-doubles, and clamps the output signal from the amplifer 44 to a reference; a non-linear network 48 for properly calibrating the scale of the measurement; and a circuit 50 for measuring the voltage of the signal.

More specifically, the rectifier and voltage-doubler 46 comprises the D.C. blocking capacitor 58, the diodes 60 and 62, and the capacitor 64 connected in the well-known manner to obtain rectification and voltage-doubling. This circuit is clearly clamped to ground potential by the diode 62.

The non-linear network 48 comprises the silicon diodes 66, 68, and 70 and the resistor 74 connected in series with each other. A shunt resistor 72 is connected across the diode 66. Diode 80 and resistor 78 shunt the output of the network. The diodes of this circuit shape the signal so that an approximately logarithmic response is obtained.

The voltage measuring circuit 50 comprises a milliammeter 82 and a calibrating resistance 76 therefor. The voltage of the resulting non-linear D.C. output from the block 48 is measured by the calibrated milliammeter.

Table I provides, by way of example only, a set of resistor and capacitor values that may be utilized to implement the present circuitry, with voltage from limiter-buffer 42 approximately 10 volts, peak-to-peak.

TABLE I

| Component | | Value |
|---|---|---|
| 58 | = | 10 microfarads |
| 64 | = | 10 microfarads |
| 72 | = | 1200 ohms |
| 74 | = | 150 ohms |
| 76 | = | 390 ohms |
| 78 | = | 220 ohms |
| 82 | = | 1 milliampere, 780 ohms |

Although the windings in the present embodiment are parallel-tuned, this is not a necessity. Series-tuned windings are equally feasible.

When designing the above set-out device, several factors should be kept in mind. For example, if the circuit components are chosen so that the operating frequency must be high to achieve the desired frequency response, then eddy current effects will predominate over magnetic effects, and the required coupling increase for a magnetic substrate will not hold true. But, if the frequency is kept too low, the circuit components tend to become quite bulky, and various practical factors make it difficult to achieve sharp tuning. A frequency on the order of 1000 hertz was used in the present design with success.

Various other circuit options may be utilized in designing a device based on the above set-out principles. For example, stagger-tuning circuitry, or Q-varying circuitry, or additional tuning elements might be added. Such variations are merely refinements of the basic principle.

A basic problem arises in the interpretation of the voltage measurements in that, depending on the drive frequency chosen, it will frequently not be clear whether the reading is from the right, or high-frequency, side of the magnetic hump 32 of FIG. 4 or from the left, or low-frequency, side of the conductive, non-magnetic hump 34. For example, if the center frequency A for the open gap hump 30 is chosen as the drive frequency, then the voltmeter will read a maximum with the instrument uninfluenced (open gap) and the reading will decrease with either magnetic or non-magnetic materials in the gap. This potential reading ambiguity requires a knowledge of the material under the coating. Furthermore, evan a minor adjustment of the VCO can cause the actual drive frequency to be at either frequency B or C in FIG. 4, thus causing the reading to increase and then decrease under some circumstances. The frequencies B and C could, of course, be used, but they would work well only over one type of substrate (non-magnetic for B, magnetic for C).

The frequency D, though seemingly a good choice for measurements over magnetic materials, has the disadvantage that, when the coating is very thin, the precise characteristics of the coating material have a significant influence on the height and location of the hump 32 of FIG. 4. Thus the calibration for thin coatings is unreliable. The frequencies E and F combine the disadvantage of frequency D with an assured ambiguity.

In order to remove this ambiguity in the readings and increase the coating thickness range of the device the drive frequency may be made variable. This, of course, could be accomplished by varying the frequency of the output signal from the VCO 40 by hand. This method of variation is inconvenient and subject to inherent inaccuracies.

The present embodiment accomplishes this drive-frequency variation by means of a feedback circuit which makes the drive frequency a function of the output voltage from the secondary winding 20. The feedback circuit comprises an adjustable isolation amplifier 54 which takes a signal from the measuring circuitry 45 and applies it, after amplification, to the frequency control input of the VCO 40. More specifically, the signal that is taken is the rectified and voltage-doubled D.C. signal from the point 61 in the block 46.

Figure 8A:
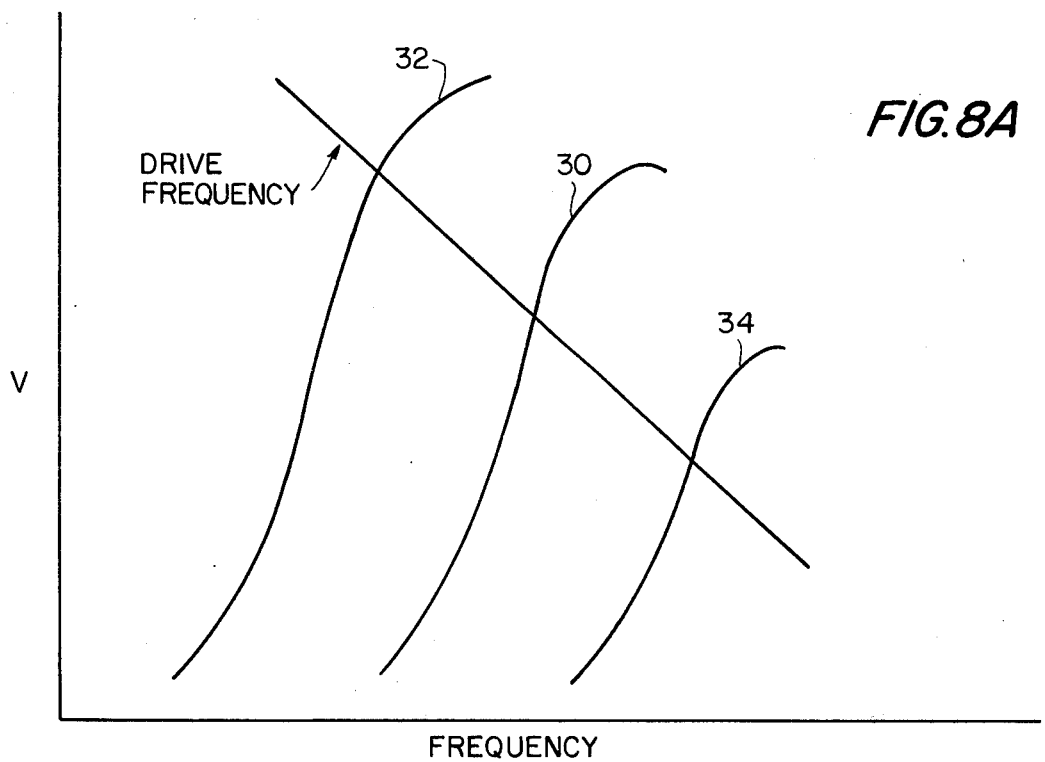
FIG. 8a is a voltage vs. frequency graphical representation of the circuit of FIG. 3 showing only the left side of the gap curves of FIG. 4 with the drive frequency superimposed thereon.
Figure 8B:
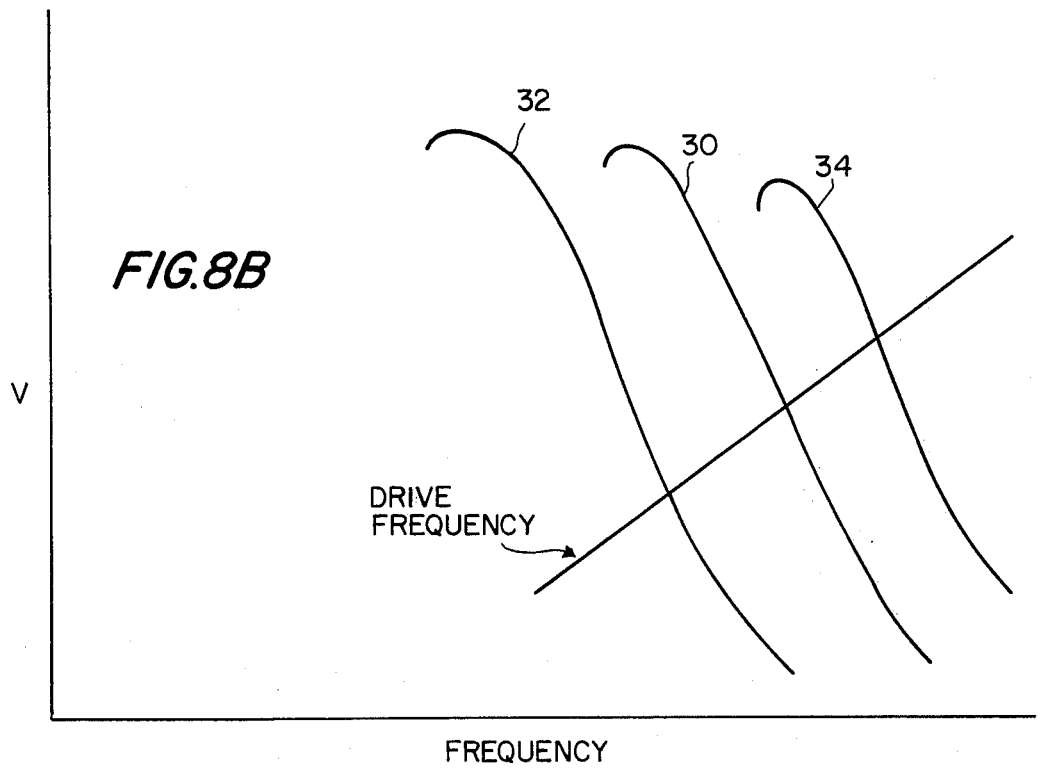
FIG. 8b is a voltage vs. frequency graphical representation of the circuit of FIG. 3 showing only the right sides of the gap curves of FIG. 4 with the drive frequency superimposed.

The addition of this feedback circuit allows the initial drive frequency (open gap) to be set at either frequency E or F in FIG. 4. This is advantageous because the ambiguous apex of the hump 30 is avoided. More importantly, when a frequency part way down the hump 30 is chosen, then the shape of the drive frequency curve can be adjusted by the feedback so that it always intersects the shifting response curves 32 and 34 on a selected side of the humps. This is shown in FIGS. 8a and 8b. If the left, or low-frequency, side of the hump is chosen, then the feedback circuit is set to decrease the drive frequency for an increasing voltage response and likewise, to increase the drive frequency for a decreasing voltage response (FIG. 6a). If the right, or high-frequency, side of the hump is chosen, then the feedback circuit is designed to increase the drive frequency for an increasing voltage response (FIG. 6b) and vice versa. Thus, where the left side of the hump is used, the voltage will always increase with a decreasing coating thickness over a magnetic substrate (steel) and will always decrease for decreasing coating thickness over a conductive, non-magnetic substrate. This relationship is exactly reversed when the right side of the hump is made significant. This approach allows a single calibration scale to be used, with one side of the center indicating a coating thickness over a magnetic substrate, and the other side indicating a coating thickness over a conductive, non-magnetic substrate. Thus both the coating thickness and the magnetic character of the substrate can be determined in one operation without ambiguity.

Generally, to operate with a variable drive frequency, a feedback circuit is required which is capable of making an approximately 20% frequency shift from the initial drive frequency.

An auxiliary voltmeter may be used in the initial design in order to develop a temporary calibration chart from which a suitable non-linear calibrating network 48 can be designed to give a convenient calibration scale for the milliammeter. The resulting scale should have a zero at each end and an infinity point near the middle. One side of the scale indicates the thickness of coatings over a magnetic substrate, while the other side indicates the coating thickness over a conductive, non-magnetic substrate.

The use of a variable frequency which is dependent on the coating thickness as described makes it possible to derive a thickness reading from the frequency, by use of a frequency-to-voltage converter (e.g., a discriminator or other frequency-modulation detector) and a calibrated voltmeter, or by merely measuring the frequency and converting the thickness by using a calibration chart. Although cumbersome, this approach would offer advantages in some applications, such as remote-reading indicators.

The span of the yoke or core should be about twice the maximum thickness to be measured. The length of the pole pieces is not critical, but should be about the same as the span, if convenient. If the pole pieces are too short, it will be difficult to achieve large coupling factors. The size and geometry will naturally influence the final calibration of the instrument.

It should be understood, of course, that although the frequencies E and F on the curve 30 are clearly the most advantageous choices for the initial drive frequency since they allow all measurements to be made on a single scale, the drive frequency could be set much higher or lower on the curve and the device specialized for either a magnetic or a conductive, non-magnetic substrate. For example, if the device is to be specialized for steel substrate, then the drive frequency may be set high on the right slope of the curve 30 or low on the left side of the curve 30. Likewise, if the device is to be specialized for aluminum substrates, then the drive frequency may be set low on the right side of the curve 30 or high on the left side.

It should further be understood that although the measuring circuitry 45 is exemplified as a milliammeter fed by a non-linear network in the present embodiment, the invention is not limited thereto. There are a wide variety of measuring techniques for processing electrical signals and extracting information therefrom which might be utilized in place of the present measuring circuitry.

The invention is capable of a large number of diverse applications. For example, if the transformer core of the probe is made on the order of an inch square, then thin coatings such as paint layers may be measured. If the pole-to-pole core size in the probe is on the order of three inches square, then deck tile, terrazzo and other materials of similar thickness may be measured. If a large probe is developed with a pole-to-pole core size on the order of a six inch square, then the depth, orientation, and spacing of reinforcement rods in concrete or the thickness of a blacktop coating over a steel bridge might be measured. If fact, if a very low drive frequency is used so that eddy currents in the plating do not interfere with the measurement, then the thickness of conductive, non-magnetic plating lying over a steel substrate might be measured.

In summary, the present over-coupled, double-tuned, open-core transformer design, due to its ability to vary its overall frequency response in accordance with changes in its self and mutual inductance, has the ability to measure coating thicknesses over either conductive, non-magnetic or magnetic substrates. This can be done on a single scale which indicates both the thickness of the coating and the magnetic identity of the substrate without any change in the instrument. With an appropriate non-linear network, this scale may made approximately logarithmic with a nearly constant percent accuracy over a wide range.

Obviously, many modifications and variations of the present invention are possible in light of the above teachings. It is therefore to be understood that, within the scope of the appended claims, the invention may be practiced otherwise than as specially described.

What is claimed is:

1. An electronic coating guage for measuring the thickness of a coating on a conductive, non-magnetic or magnetic substrate comprising:
    double-tuned over-coupled transformer means with a primary and a secondary winding each tuned to the same frequency, said transformer means having a U-shaped core which is adapted to have its open face flush with the coating of the substrate to be tested;
    A.C. input means for applying an A.C. signal to said primary winding; and
    means for measuring the voltage response at said secondary winding of said transformer means;
    said measuring means providing changes in the resonant frequency response characteristics of said transformer, which changes are indicative of the thickness of said coating.

2. An electronic coating gauge as defined in claim 1, wherein said A.C. input means comprises:
    voltage-controlled-oscillator means for applying an A.C. signal to said primary winding; and
    feedback means taking a signal from said voltage-measuring means and applying it to said voltage-controlled-oscillator means to control the frequency of the A.C. output therefrom in accordance with the increases and decreases of the signal from said voltage measuring means.

3. An electronic coating gauge as defined in claim 1, wherein said voltage-measuring means comprises:
    means for rectifying the A.C. voltage response;
    non-linear conversion means for converting the signal from said rectifying means to a suitable scale; and
    milliammeter means for measuring the voltage from said non-linear conversion means.

4. An electronic coating guage as defined in claim 2, wherein the frequency of said voltage-controlled oscillator is measured and converted to a thickness measurement.

* * * * *